United States Patent [19]

Chelberg et al.

[11] Patent Number: 5,082,926
[45] Date of Patent: Jan. 21, 1992

[54] POLYPEPTIDE WITH TYPE IV COLLAGEN CELL ADHESION, SPREADING AND MOTILITY ACTIVITY

[75] Inventors: Mary K. Chelberg; Photini-Effie C. Tsilibary; James B. McCarthy, all of Minneapolis, Minn.

[73] Assignee: Regents of the University of Minnesota, Minneapolis, Minn.

[21] Appl. No.: 450,419

[22] Filed: Dec. 14, 1989

[51] Int. Cl.$^5$ .................... C07K 7/08; A61K 37/00
[52] U.S. Cl. .................................................... 530/326
[58] Field of Search ............. 530/326, 325, 324, 350; 514/14, 13, 12

[56] References Cited

U.S. PATENT DOCUMENTS 4,876,332 10/1989 Tsilibary et al. .............. 530/326

OTHER PUBLICATIONS

Glanville et al., Eur. J. Biochem., 152, 213-219, (1985).
Brazel et al., Eur. J. Biochem., 168, 529-536, (1987).
Brinker et al., Proc. Natl. Acad. Sci. U.S.A., vol. 82, pp. 3649-3653, (1985).
Pihlajaniemi et al., J. Biol. Chem., vol. 260, No. 12, pp. 7681-7687, (1985).
R. Timpl et al., *Macromolecular Organization of Type IV Collagen*, in *New in Basement Membrane Research*, Raven Press, N.Y., 57-67 (1982).
J. Murray et al., *J. Cell Biol.*, 80, 197-202 (1979).
M. Aumailley et al., *J. Cell Biol.*, 103, 1569-1576 (1986).
T. Herbst et al., *J. Cell Biol.*, 106, 1365-1373 (1988).
M. Kurkinen et al., *J. Biol. Chem.*, 259, 5915-5922 (1984).
S. Sugrue, *J. Biol. Chem.*, 262, 3338-3343 (1987).
K. Tomaselli et al., *J. Cell Biol.*, 105, 2347-2358 (1987).
J. Oberbaumer et al., *Eur. J. Biochem.*, 147, 217-224 (1985).
U. Schwarz-Magdolen et al., *Febs. Lett.*, 208, 203-207 (1986).
D. Brazel et al., *Eur. J. Biochem.*, 172, 35-42 (1988).
R. Soininemi et al., *Febs. Lett.*, 225, 188-194 (1987).
G. Muthukamaran et al., *J. Biol. Chem.*, 264, 6310-6317 (1989).
J. Saus et al., *J. Biol. Chem.*, 264, 6318-6324 (1989).
G. Koliakos et al., *J. Biol. Chem.*, 264, 2313-2323 (1989).
W. Babel et al., *Eur. J. Biochem.*, 143, 545-556 (1984).
E. Tsilibary et al., *J. Cell Biol.*, 103, 2467-2473 (1986).
E. Tsilibary et al., *J. Biol. Chem.*, 263, 19112-19118 (1988); and
M. Chelberg et al., *Cancer Research*, 49, 4796-4802 (1989).

Primary Examiner—Lester L. Lee
Assistant Examiner—Avis Davenport
Attorney, Agent, or Firm—Merchant, Gould, Smith, Edell, Welter & Schmidt

[57] ABSTRACT

A polypeptide having the following formula is provided: gly-val-lys-gly-asp-lys-gly-asn-pro-gly-trp-pro-gly-ala-pro which has the ability to promote cellular adhesion, spreading the motility, while remaining highly cell specific. Medical applications such as chemodiagnostic and chemotherapeutic devices are also provided.

2 Claims, 8 Drawing Sheets

FIG. 2

```
M MGPRLSVVLLLLPAALLLHEERSRAAAKGDCCGSCCGKCDCHCVKCQKGERCGLPGLQGVIGFPGMQGPEGPEGPPGQKGDAGEPGLPGTKGTRGPPGAAG 100
  |||||||||||||| |||||||||| ||||||| | |||||||||||||||||||||||||| || |||||||||| |||||||||||||||||||| |
H MGPRLSVVLLLLPAALLLHEERSRAAAKGGCAGSGCGKCDCHCVKCQKGERCGLPGLQGVIGFPGMQGPEGPQGPPGQKGDTGEPGLPGTKGTRGPPGASG 100

7S→ ┌1┐
  YPGNPGLPGIPGQDGPPGPPGIPGCNGTKGERGPLGPPGLPGTSGNPGPPGLPGMKGDPGEILGHVPGTLLKGERGFPGIPGMPGSPGLPGLQGPVGPPG 200
  |||||||||||||||||||||||||||||||||||||||||||||| ||||||||||||||||||||| |||||||||||| |||||||||||||||
  YPGNPGLPGIPGQDGPPGPPGIPGCNGTKGERGPLGPPGLPGTVGNPGPPGLPGMKGDPGEILGHVPGMLLKGERGFPGIPGTPGPPGLPGLQGPVGPPG 200

┌2┐            ┌──3──┐         ┌4┐
  FTGPPGPPGPPGPPGEKGQMGSSPQGPKGDKGDQGVSCPPGVPGQADVKEKGDFAPTGEKGQKGEPGFPGVHGTLEKGEPGKQGPRGKPGKDGEKGERGS 300
  |||||||||||||||||||||||| |||||||||||||||||||| ||||||||||||||||||||| |||| ||||||| |||||||||||||||
  FTGPPGPPGPPGPPGEKGQMGLSPQGPKGDKGDQGVSCPPGVPGQADVQEKGDFATKGEKGQKGEPGFQGMEGVEKGEPGKPGPRGKPGKDGDKGEKGS 300

┌5┐                         ┌6┐
  PGIPGDSGYPGLPGRQGPQGEKGEAGLPGPPGTVIGTMPLGEKGDRGYPGAPGLRGEPGPKGFPGTPGQPGPPGFHITPQAGAPGFPGERGEKGDQGFPG 400
  || ||||| |||||||||||||||||||||||| ||| |||||||||||||| ||||||||||| |||||||| | |||||||||||||||| ||||
  PGFPGEPGYPGLIGRQGPQGEKGEAGPPGPPGCIVLGTEPLGEKGERGYPGTPGPRGEPGPKGFPGLPGQPGPPGLNFCQAGAPGFPGERGEKGDRGFPG 400

┌7┐                               ┌──8──┐                                 ┌─9─┐
  VSLPGPSGRDGAPGPPGPPGPPGQPGEHDGIVECQPGPPGDQGPPGTPGQPGCLTGEVGQKGQKGESCLACDTECLRGPPGPQGPPGEIGFPGQPGAKGDR 500
  ||| ||||||| |||||| |||||||||| |||||||| ||||||| | |||||| || |||||||| ||| ||| |||||||||||||||||||||
  TSLPGPSGRDGLPGPPGSPGPPGQPGCTNGIVECQPGPPGDQGPPGIPGQPGFIGEIGEKGQKGESCLICDILCYRGPPGPQGPPGEIGFPGQPGAKGDR 500

┌───10───┐
  GLPGRDGLEGLPGPQGSPGLIGQPGAKGEPGEIFDMILGDKGDPGYPGQPGMPGRAGTPGRDGHPGLPGPKGSPGSIGLKGERGPPGGVGFPGCSRGDI 600
  ||||||| | |||||||||||||||||||||| ||||||||||||||||||| |||| ||||||||||||||||||| ||||||||||||||||
  GLPGRDGVACVPGPQGTPGLIGQPGAKGEPGEIFYDLRLGDKGDPGYPGQPGMPGRACSPGRDGHPGLPGPKGSPGSVGLKGERGPPGGVGFPGCSRGDT 600

┌11┐                 ┌12┐                                          ┌13┐
  GPPGCPGVGPIGPVGEKGQAGFPGGPGSPGLPGPKGEAGKVPLFCPPGAAGLPGSPGFPGPQGDRGFPGTPGRPGIPGEKGAVGQPCIIFPGLPGPKGV 700
  |||||| ||| | ||||||||||||||||||||||||||| ||| |||| |||||| |||||||||||||||||||||||||||||| | |||||||
  GPPGPPGVGPAGPIGDKGQAGFPGGPGSPGLPGPKGEPGKIVPLFCPPGAEGLPGSPGFPGPQGDRGFPGTPGRPGLPGEKGAVGQPCIIFPGPPGPKGV 700

┌14┐                                                              ┌15┐
  DGLPGEIGRPGCSPGRPGFNGLPGNPGPQGQKGEPGICLFGLKGQPGLPGIPGTPGEKGSIGCPGVPGEDQGLTGPPGLQGIRGDPGPPGCVQGPAGPPGCVRC 800
  |||||| | ||| | ||||||||||||||||||||||||| ||| ||||||||||||||||| |||||||| ||||| ||||| | ||||||||||
  DGLPGDMGPPGTPGRPGFNGLPGNPCVQGQKGEPGVGLFGLKGLPGLPGIPGTPGEKGSIGVPGVPGEEGAIGPPGLQGIRGEPGPPGLPGSVGSPGCVRC 800
```

FIG. 2 CONTINUED

```
IGPPGAMGPPGGEGPPGSSGPPGIKGEKGFPGFPGLDMPGPKGDKGSQGLPGCLTGQSGLPGLPGQQGTPGVPGFPGSKGEMGVMGTPGQPGSPGPAGTPG  900
|||||||| ||||||||||||||||||||||||||||| |||||||||||||||||||||||||||||||||||||||||||||||||||||||| ||
IGPPGARGPPGGQGPPGLSGPPGIKGEKGFPGFPGLDMPGPKGDKGAQGLPGITGQSGLPGLPGQQGAPGIPGFPGSKGEMGVMGTPGQPGSPGPVGAPG  900

LPGEKGDHGLPGSSGPRGDPGFPGDKGDVGLPGHPGSHEHVDMGSMKCQKGDQGEKGQIGPTCDKGSRGDPGTPGVPGCKDGQAGHPGQPGPKGDPGLSGT 1000
||||||||| |||  |||||||||||||||||||||| |||||||||||||||||||||||| |||||||||||||||||||| ||||||||| |||
LPGEKGDHGFPGSKGPRGDPGLKGDKGDVGLPGKPGSHDKVDMGSMKCQKGDQGEKGQIGPIGEKGSRGDPGTPGVPGCKDGQAGQPGQPGPKGDPGISGT 1000

PGSPGLPGPKGSVGGMGLPGSPGEKGVPGIPGSQGVPGSPGEKGAKGEKGQSGLPGIGIPGIPGDKGDQGLAGYPGSPGEKGEKGSAGTPGMPGSPGPRG 1100
|| ||||| |||||||||||| |||||| || ||||||||||||||||||| ||||||||||| |||||||||||||||||||||| ||||||| |
PGAPGLPGPPGSVGGMGLPGTPGEKGVPGIPGPQGSPGLPGDKGAKGEKGQAGPFGIGIPGLKGEKGDQGIAGYPGSPGEKGEKGSIGIPGMPGSPGLKG 1100

SPGMIGHPGSPGLPGEKGDKGLPGLDGVPGVKGEAGLPGTPGPTGPAGQKGEPGSDGIPGSAGEKGEQGVPGMGYPGFPGSKGDKGSKGEVGFPGLAGSP 1200
|||  | |||||||||||||||||||| ||||||||||||||||||||||||||||||||||||||||||    |||||| |||||||||||||||||
SPGSVGYPGSPGLPGEKGDKGLPGLDGIPGVKGEAGLPGTPGPTGPAGQKGEPGSDGIPGSAGEKGEPGLPGMGYPGFPGAKGDKGSKGEVGFPGLAGSP 1200

GIPGVKGEQGFMGPPGPQGQPGLPGTPGHPVEGPKGDRGPQGQPGLPGHPGPMGPPGFPGINGPKGDKGMQGWPGAPGVPGPKGDPGPQGMPGIGGSPGI 1300
|||| |||||||||||||||||||||||||  |||||||||||||||||||||||||||||| ||||||||||||||||||||||||||||||||||
GIPGSKGEQGFMGPPGPQGQPGLPGSPGHATEGPKGDRGPQGQPGLPGLPGPMGPPGLPGIDGVKGDKGMPGWPGAPGVPGPKGDPGPQGMPGIGGSPGI 1300

TGSKGDMGLPGVPGFQGQKGLPGLQGVKGDQGDQGVPGPKGLPGPPGPPGPMDVIKGEPGLPGPEGPPGLKGLQGPPGPKGQQGVTGSVGLPGPPGVPGF 1400
|||||||| ||||||||  |||||||| |||||||| ||||||||||||| ||| ||||||||||||||||| |||||||||||||| ||||| || |
TGSKGDMGPPGVPGPGPQGPKGLPGLQGIKGDQGDQGVPGAKGLPGPPGPPGPDIIKGEPGLPGPEGPPGLKGLQGLPGPKGQQGVTGLVGIPGPPGIPGF 1400
                                        NC1*
DGAPGQKGETGPFGPPGPRGFPGPPGPDGLPGSMGPPGCTPSVDHGFLVTRESQTTDDPLCPPGTKILYBGYSLLYVQGMERAHGQDLGTAGSCLRKFSTM 1500
|||||||| || || |||||||||||||||||||||||||||||| ||||||||| ||| |||||||||||||||||||||||||||||||||||||
DGAPGQKGEMGPAGPTGPRGFPGPPGPDGLPGSMGPPGCTPSVDHGFLVTRESQTIDDPQCPSGTKILYBGYSLLYVQGMERAHGQDLGTAGSCLRKFSTM 1500

PPLPCMIMNVCNFASRNDYSYVLSTPEPMPMSHAPISGDNIRPFISRCAVCEAPAMVMAVBSQTIQIPQCPWGMSSLWIGYSFVMHTSAGAEGSGQALAS 1600
||||||||||||||||||||||||||||||||| ||| ||||||||||||||||||| ||||||||| ||||||||||||||||||||||||||||||
PPLPCMIMNVCNFASRNDYSYVLSTPEPMPMSHAPITGENIRPFISRCAVCEAPAMVMAVBSQTIQIPPCPSGMSSLWIGYSFVMHTSAGAEGSGQALAS 1600

PGSCLEEFRSAPFIECBGRGTCMYYANAYSFWLATIERSEMFKKPTPSTLKAGELRTHVSRCQVCMRRT 1699
|||||||||||||||||||||||||||||||||||||||||||||||||||||||||||||||||||
PGSCLEEFRSAPFIECBGRGTCMYYANAYSFWLATIERSEMFKKPTPSTLKAGELRTHVSRCQVCMRRT 1699
```

POLYPEPTIDE WITH TYPE IV COLLAGEN CELL ADHESION, SPREADING AND MOTILITY ACTIVITY

GOVERNMENT SUPPORT

This invention was made with government support under contract Nos. CA 43924 and 39216 by the U.S. Institutes of Health. The government has certain rights in the invention.

BACKGROUND OF THE INVENTION

Type IV collagen is a distinctive glycoprotein which occurs almost exclusively in basement membranes, structures which are found in the basal surface of many cell types, including vascular endothelial cells, epithelial cells, etc. Type IV collagen is a major component of basement membranes. It differs from interstitial collagens. See *New Trends in Basement Membrane Research*, K. Kuehn et al., eds., Raven Press, N.Y., at pp. 57-67 (1982). Type IV collagen has a molecular weight (MW) of about 500,000 and consists of three polypeptide chains: two $\alpha 1$ (MW 185,000) chains and one $\alpha 2$ (MW 170,000) chain. Type IV collagen has two major proteolytic domains: a large, globular, non-collagenous, NCl domain and another major triple-helical collagenous domain. The latter domain is interrupted by non-collagenous sequences of variable length. A diagrammatic representation of the type IV collagen molecule is shown in FIG. 1. It is a complex and multidomain protein with different biological activities residing in different domains.

Type IV collagen self-assembles to polymeric structures which constitute the supportive frame of basement membranes. Various other macromolecular components bind to type IV collagen, such as: laminin, entactin/nidogen and heparin sulfate proteoglycan. An additional function of type IV collagen is to mediate cell binding. A variety of cell types specifically adhere and spread onto type IV collagen-coated substrata. See J. C. Murray et al., *J. Cell Biol.*, 80, 197-202 (1979); M. Aumailley et al., *J. Cell Biol.*, 103, 1569-1576 (1986); T. J. Herbst et al., *J. Cell Biol.* 106, 1365-1373 (1988). Various cell surface proteins, a 47 kD protein [M. Kurkinen et al., *J. Biol. Chem.*, 259, 5915-5922 (1984)], a 70 kD protein [S. P. Sugrue, *J. Biol. Chem.*, 262, 3338-3343 (1987)] and members of the superfamily of integrins [K. J. Tomaselli et al., *J. Cell Biol.*, 105, 2347-2358 (1987)], have been reported to mediate cell binding to type IV collagen.

The variety of functions of type IV collagen suggests that this glycoprotein is important in many diverse and clinically relevant processes such as cell attachment and migration in wound healing, tumor cell invasion and metastasis, diabetic microangiopathy, vascular hypertrophy due to hypertension and several kidney diseases such as diabetic nephropathy and nephrotic syndromes of variable etiology. For example, in Goodpasture's syndrome, a disease characterized by hemoptysis and hematuria due to alveolitis and nephritis, respectively, an antibody to the major noncollagenous NCl domain of type IV collagen is found in the serum of all Goodpasture's patients. Another hereditary kidney disease, Alport's familial nephritis, is apparently due to a genetic defect of the NCl domain of type IV collagen. In addition, in diabetes mellitus, intact type IV collagen, as well as the triple helix-rich domain, are chemically modified and functionally impaired by the increased amounts of glucose present in the plasma and in the immediate vicinity of the basement membranes, i.e., in the extracellular matrix.

In order to better understand the pathophysiology of these processes at a molecular level, there is a need to try to assign at least several of the above-mentioned biological activities of type IV collagen to the specific proteolytic domains (i.e., NCl, triple helix-rich domains) or oligopeptides of type IV collagen. If this can be achieved, it will be possible to synthesize small peptides which can provide the basis for important pharmaceutical compositions.

BRIEF DESCRIPTION OF THE INVENTION

The present invention provides a polypeptide (hereinafter designated "IV-H1") which represents a fragment of the $\alpha 1$ chain of human type IV collagen derived from the continuous collagenous region of the major triple helical domain. This polypeptide can be prepared by conventional solid phase synthesis. The formula of the polypeptide is:

gly—val—lys—gly—asp—lys—gly—asn—pro—gly—trp—pro—gly—ala—pro

Polypeptide IV-H1 formally represents isolated type IV collagen residues 1263-1277 from the major triple helical region of the $\alpha 1$ chain of type IV collagen. The single letter amino acid code for this polypeptide is GVKGDKGNPGWPGAP.

This synthetic polypeptide was assayed for biological activity and found to promote the adhesion and spreading of many cell types, and was a potent attractant for melanoma cell motility. In addition, peptide IV-H1 is highly specific in its cell binding properties. For example, the peptide promotes binding of nerve cells, but not of endothelial cells. Therefore, it is believed that polypeptide IV-H1 may be useful to (a) promote cellular attachment to culture substrata, and (b) inhibit the metastasis and invasion of tumor cells. Since certain cell types have been shown or are expected to have cell specific binding behavior in response to peptide IV-H1, other uses of this peptide are envisioned, such as assistance in nerve regeneration and diagnostic use. Furthermore, since it is expected that further digestion/hydrolysis of peptide IV-H1 in vitro or in vivo will yield some fragments of substantially equivalent bioactivity, such lower molecular weight peptides are also considered to be within the scope of the present invention.

BRIEF DESCRIPTION OF THE DRAWINGS

FIG. 2 depicts the primary amino acid sequence of the human and murine $\alpha 1$ chain of type IV collagen in comparison.

DETAILED DESCRIPTION OF THE INVENTION

Figure 1:
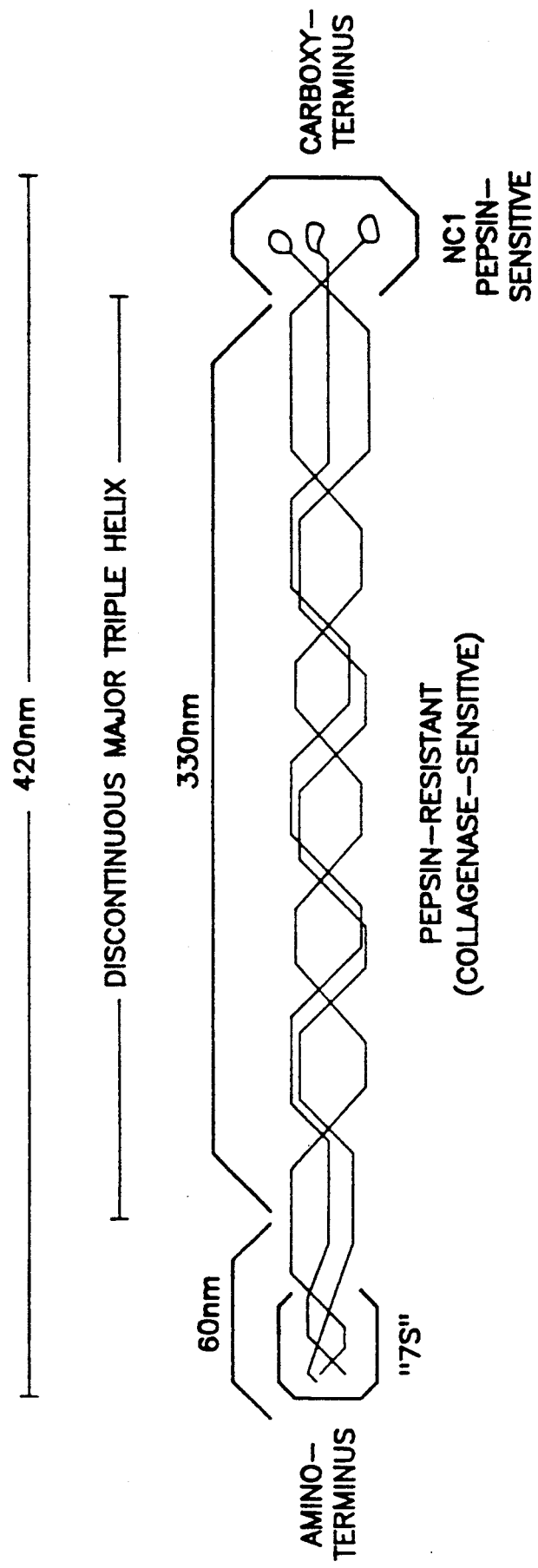
FIG. 1 is a diagrammatic representation of type IV collagen, indicating the structure of the $\alpha 1$(IV) and $\alpha 2$(IV) chains, each with a major non-collagenous, NCl domain and the triple helix-rich domain containing interruption of the gly-X-Y triple helical motif.

The structure of the two α1 chains and the single α2 chain of type IV collagen, has been the subject of much study. See J. Oberbaümer et al., *Eur. J. Biochem.*, 147, 217-224 (1985); T. Pihlajanien et al., *J. Biol. Chem.*, 260 7681-7687 (1985); U. Schwarz-Magdolen et al., *Febs. Lett.*, 208, 203-207 (1986); D. Brazel et al., *Eur. J. Biochem.*, 172, 35-42 (1988); R. Soininemi et al., *Febs. Lett.*, 225, 188-194 (1987); D. Brazel et al., *Eur. J. Biochem.*, 168, 529-536 (1987); G. Muthukamaran et al., *J. Biol. Chem.*, 264, 6310-6317 (1989); J. Saus et al., *J. Biol. Chem.*, 264, 6318-6324 (1989). The sequence of the α1 chain is shown in FIG. 2. The total number of amino acids per collagen molecule is approximately 4,550, with each α1(IV) chain containing approximately 1,390 amino acids.

U.S. Pat. No. 4,876,332 describes three peptides (designated "TS-1, TS-2 and TS-3") from the NC1 domain of the α1 (IV) chain of type IV collagen that promote adhesion of a number of cell types, including aortic endothelial cells and metastatic carcinoma cells. Two of these peptides (TS-2 and TS-3) also bind to heparin.

Peptide IV-H1 described herein is derived from the pepsin generated major triple helical fragment of type IV collagen. Peptide IV-H1 promotes cell adhesion and spreading and is a potent attractant for M4 melanoma tumor cell motility. However, peptide IV-H1 does not bind heparin. See G. F. Koliakos et al., *J. Biol. Chem.*, 264, 2313-2323 (1989). Importantly, it has been found that peptide IV-H1 only promotes adhesion of certain specific cell types such as melanoma and nerve cells, but not endothelial or fibrosarcoma cells.

SYNTHESIS OF THE POLYPEPTIDE

The polypeptide of the invention was synthesized using the Merrifield solid phase method. This is the method most commonly used for peptide synthesis, and it is extensively described by J. M. Stewart and J. D. Young in *Solid Phase Peptide Synthesis*, Pierce Chemical Company, pub., Rockford, Ill, (2nd ed., 1984), the disclosure of which is incorporated by reference herein.

The Merrifield system of peptide synthesis uses a 1% crosslinked polystyrene resin functionalized with benzyl chloride groups. The halogens, when reacted with the salt of a protected amino acid will form an ester, linking it covalently to the resin. The benzyloxycarbonyl (BOC) group is used to protect the free amino group of the amino acid. This protecting group is removed with 25% trifluoroacetic acid (TFA) in dichloromethane (DCM). The newly exposed amino group is converted to the free base by 10% triethylamine (TEA) in DCM. The next BOC-protected amino acid is then coupled to the free amino of the previous amino acid by the use of dicyclohexylcarbodiimide (DCC). Side chain functional groups of the amino acids are protected during synthesis by TFA stable benzyl derivatives. All of these repetitive reactions can be automated, and the peptides of the present invention were synthesized at the University of Minnesota Microchemical facility by the use of a Beckman System 990 Peptide synthesizer.

Following synthesis of a blocked polypeptide on the resin, the polypeptide resin is treated with anhydrous hydrofluoric acid (HF) to cleave the benzyl ester linkage to the resin and thus to release the free polypeptide. The benzyl-derived side chain protecting groups are also removed by the HF treatment. The polypeptide is then extracted from the resin, using a 1.0M acetic acid, followed by lyophilization of the extract. Lyophilized crude polypeptides are purified by preparative high performance liquid chromatography (HPLC) by reverse phase technique on a C-18 column. A typical elution gradient, such as used in the present case, is 0% to 60% acetonitrile with 0.1% TFA in $H_2O$. Absorbance of the eluant is monitored at 220 nm, and fractions are collected and lyophilized.

Characterization of the purified polypeptide is by amino acid analysis. The polypeptides are first hydrolyzed anaerobically for 24 hours at 110° C. in 6M HCl (constant boiling) or in 4 N methanesulfonic acid, when cysteine or tryptophane are present. The hydrolyzed amino acids are separated by ion exchange chromatography using a Beckman System 6300 amino acid analyzer, using citrate buffers supplied by Beckman. Quantitation is by absorbance at 440 and 570 nm, and comparison with standard curves. The polypeptides may be further characterized by sequence determination. This approach is especially useful for longer polypeptides, where amino acid composition data are inherently less informative. Sequence determination is carried out by sequential Edman degradation from the amino terminus, automated on a Model 470A gas-phase sequenator (Applied Biosystems, Inc.), by the methodology of R. M. Hewick et al., *J. Biol. Chem.*, 256, 7990 (1981).

The peptide of the invention, IV-H1 (GVKGDKGNPGWPGAP), was synthesized from the sequence of the major triple helical domain of human type IV collagen. As a further control, other type IV collagen-derived peptides from the major triple helical domain were synthesized and studied (See Table 1). Certain of the peptides were synthesized with a tyrosyl residue to the carboxy terminal end to allow radioactive iodination of the peptide.

TABLE 1

Type IV Collagen-Derived Synthetic Peptides

| Peptide name | Peptide Sequence* | Residue Numbers@ |
|---|---|---|
| peptide 15 | GPKGEPGKIVPLPG(Y) | 634–647 |
| peptide 16 | GLPGKPGSNDKVDMGSMKG(Y) | 930–948 |
| peptide 17 | GVPGKDGQAGQPGQP(Y) | 975–989 |
| peptide 18 | GEKGDKGLPGLD(Y) | 1115–1126 |

*Using the single-letter amino acid code: A = alanine, D = aspartate, E = glutamate, G = glycine, I = isoleucine, K = lysine, L = leucine, M = methionine, N = asparagine, P = proline, Q = glutamine, S = serine, V = valine. Each peptide contained a tyrosine residue (Y) at the carboxyl terminal end so that the peptides could be iodinated.
@Residue numbers assigned beginning with amino terminal end, based upon the sequence presented in Muthukumaran, Blumberg, and Kurkinen, J. Biol. Chem., 264, 6310–6317 (1989).

Cell Culture

Highly metastatic murine melanoma cells, K-1735-M4 were originally provided by Dr. I. J. Fidler of Anderson Hospital, University of Texas Health Sciences Center, Houston, Texas. When the cells were received, a large number of early passage cells were propagated and frozen in liquid nitrogen. The tumor cells are usually cultured in vitro for no longer than six weeks, and the number of in vitro passages is limited to eight. The cells are then discarded and new cells withdrawn from storage for use in further in vitro and in vivo experiments. These precautions are taken to minimize phenotypic drift that can occur as a result of continuous in vitro passage. The cells were cultured in Dulbecco's Modified Eagle's Medium (DME) containing 10% heat inactivated fetal calf serum. The cultures were grown in 37° C. incubators with a humidified atmosphere containing 5% $CO_2$. Cells were subcultured twice weekly by releasing cells gently from the flask, using 0.05% trypsin and 1 mM EDTA as described by McCarthy et al., *Biochemistry*, 27, 1380–1388 (1988).

To characterize peptide IV-H1, the interaction of the peptide with other cell lines was investigated. These cell lines include the highly metastatic human melanoma cell line A375 M (also provided by Dr. Fidler), which was maintained in MEM with added vitamins and 10% FBS; and the fibrosarcoma cell line UV2237 MM, which was maintained in DME with 10% FBS. Other cell lines studied included: the C6 rat glioma cell line (ATCC, #CCL107), which was maintained in DME plus 10% CS; the SCC9 human squamous carcinoma cell line (ATCC, #CRL1629), which was maintained in a 1:1 solution of DME and HAM F12 containing 10% FBS; the B65 and B104 murine neuroblastoma cell lines which were obtained from Dr. David Schubert at the Salk Institute (Schuber et al., *Nature*, 249, 224–227 (1974)) and maintained in F12H media with supplements; and bovine aortic endothelial cells, which were isolated and maintained as described by Herbst et al., *J. Cell Biol.*, 106, 1365–1373 (1988), the disclosure of which is incorporated by reference herein.

PROTEIN PURIFICATION AND PREPARATION OF PROTEOLYTIC FRAGMENTS OF TYPE IV COLLAGEN

Type IV collagen was extracted from the Englebreth Holm Swarm sarcoma grown in lathyritic mice according to a modification of the method by Kleinman et al., *Biochemistry*, 21, 6188–6193 (1982), as described in Herbst et al., *J. Cell Biol.*, supra. Type IV collagen purified by DEAE anion exchange chromatography was subjected to ultracentrifugation at 110,000 X g for 90 minutes to clear aggregates greater than 50S. The supernatant was decanted and stored in 2M guanidine containing 2 mM dithiothreitol at 4° C. until needed. The concentration of type IV collagen was determined spectrophotometrically as described by Waddell, *J. Lab. Clin. Med.*, 48, 311–314 (1956) Type I collagen (Vitrogen) was obtained from the Collagen Corporation, Palo Alto, Calif.

IODINATION OF PEPTIDES AND DETERMINATION OF BINDING EFFICIENCY ON IMMULON 1 PLATES

Labeling of peptides with $Na^{125}I$ was performed as described by McCanahey and Dixon, *Methods Enzymol.*, 70, 210–213 (1980). Briefly, 0.1 mg of each peptide in $NaHPO_4$ buffer (pH 7.2) was incubated for 2 minutes with 0.05 mg chloramine T and 0.5 mCi $Na^{125}I$ (NEN Division of Du Pont Co., Boston, Mass.). The reaction was terminated by the addition of 0.2 mg of $Na_2S_2O_5$. Free iodine was removed by reverse-phase chromatography using Sep-pak C-18 columns (Waters Division of Millipore, Bedford, Mass.), from which the radiolabeled peptides were eluted with acetonitrile (50%) containing 0.1% trifluoroacetic acid. The labeled peptides were lyophilized and stored at −80° C. until needed. The efficiency of peptide binding to the wells of 96-well polystyrene Immulon 1 plates (Dynatech Laboratories, Inc., Chantilly, Va.) was determined by drying down 100 µl aliquots of radioiodinated peptides, which had been diluted in Voller's carbonate buffer to concentrations ranging from 1–10 µg/ml. In order to simulate binding conditions of the peptides in adhesion and spreading assays, the wells were then washed and incubated for 2 hours with 150 µl/well of a 10 mg/ml solution of BSA in Voller's carbonate buffer. The wells were then washed and the amount of peptides bound to the surfaces was quantitated by solubilizing the peptides with 150 µl/well of 0.5N NaOH containing 1% SDS. Bound radioactivity was quantitated in a Tm Analytic gamma counter model 1193.

The invention will be further described by reference to the following detailed examples.

EXAMPLE 1

Melanoma Cell Adhesion and Spreading on Peptide IV-H1

A number of peptides derived from the major triple helical region of human type IV collagen were synthesized as described above. These peptides, including peptide IV-H1 were screened for their ability to promote K 1735 M4 melanoma cell adhesion and spreading as follows:

Subconfluent cultures of M4 melanoma cells were radiolabeled overnight with 2 μCi/ml $^3$H-thymidine. Prior to the adhesion assay, the cells were released from the culture flasks with 10 mM EDTA in Hank's media or, alternatively, in a trypsin solution (0.05% trypsin with 0.02% EDTA) in order to confirm that cell adhesion did not require endogenous cell surface proteins which would be retained after EDTA treatment. The melanoma cells were then washed and resuspended to a final concentration of $3-4 \times 10^4$ cells/ml in DME supplemented with 20 mM Hepes and 10 mg/ml BSA. The cells remained viable (>95%) after this procedure, based upon exclusion of trypan blue dye.

Immulon 1 microtiter plates were prepared by drying down 100 μl/well of IV-H1 peptide which had been diluted to various concentrations (1-500 μg/ml) in Voller's carbonate buffer. The ability of the IV-H1 peptide to bind the plates was determined using radioiodinated peptides (described previously) in order to be certain that any differences in cell adhesion (or spreading) were not due to differential binding to surfaces. Nonspecific cell adhesion to sites on the plastic was blocked by the use of a 10 mg/ml solution of BSA in Voller's carbonate buffer at 37° C. for 1 hr. The Voller's/BSA solution was then aspirated and $5-6 \times 10^3$ M4 melanoma cells were added to each well in 150 μl of adhesion media (DME containing 20 mM Hepes and 10 mg/ml BSA). The cells were incubated for 30-40 min. at 37° C. (or up to 90 min. for certain assays), at which time cells were either visualized for spreading or harvested to determine adhesion. Adhesion was quantitated after washing to remove nonadherent and weakly adherent cells, by solubilizing the cells with 150 μl/well of 0.5N NaOH containing 1% SDS. Bound radioactivity was quantitated in a Beckman LS 3801 liquid scintillation counter. Spreading determinations were made by two different individuals, in double blind studies by visualizing at least 100 cells/well and calculating the percentage of spread cells. Each experiment was repeated a minimum of three times, and within a given experiment, each experimental point was determined in triplicate.

Figure 3A:
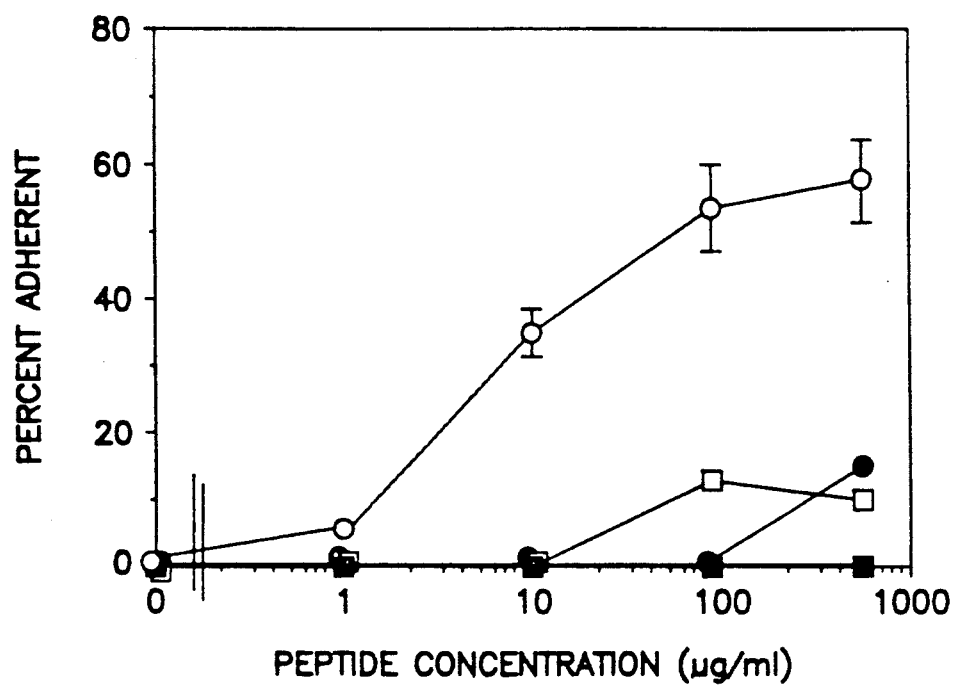
FIG. 3a is a graph showing the percent melanoma cell adhesion per concentration of peptide IV-H1 (○), and control peptides 15 (■), 17 (•) and 18 (□), coated on Immulon I wells.
Figure 3B:
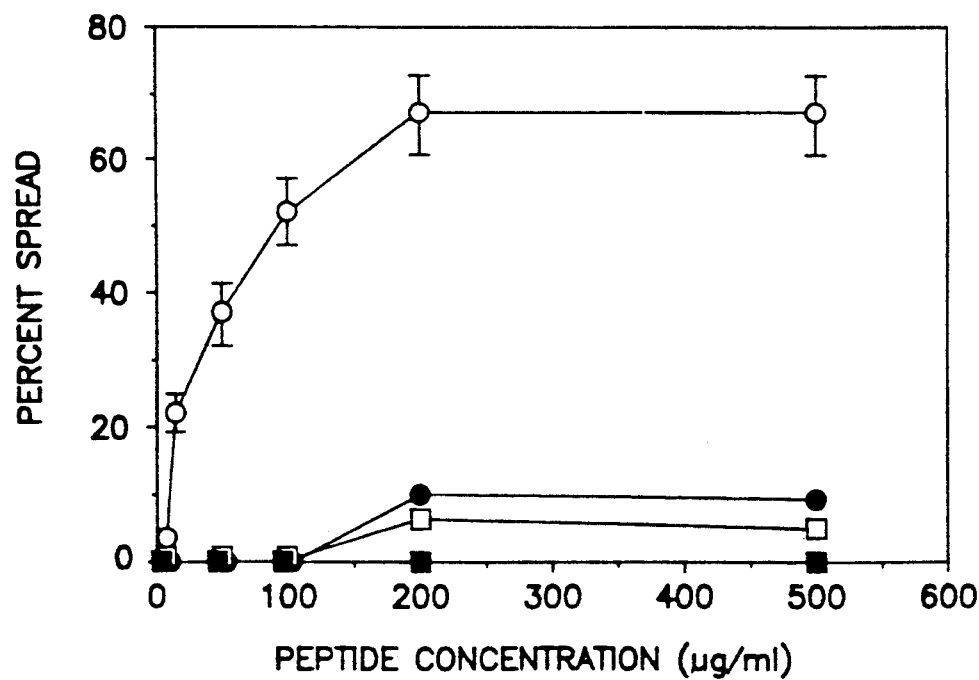
FIG. 3b is a graph showing the percent of melanoma cell spreading per concentration of peptide IV-H1 (○), and control peptides 15 (■), 17 (•) and 18 (□), coated on Immulon I wells.

The IV-H1 peptide promoted melanoma cell adhesion in a concentration-dependent manner within a coating range of 1-500 μg/ml (FIG. 3a). Significant cell adhesion (35% of input cells) occurred at a coating concentration of 10 μg/ml of peptide IV-H1 and maximal cell adhesion (>50% of input cells) was observed in wells coated with a 100 μg/ml solution of peptide IV-H1. Also, melanoma cell spreading occurred on surfaces coated with peptide IV-H1 in a concentration-dependent manner. Maximal spreading (approximately 70% of input cells) was observed within 40 min. at the 100 μg/ml coating concentration of peptide IV-H1 (FIG. 3b).

EXAMPLE 2

Comparative Adhesion and Spreading of Various Cell Types on Peptide IV-H1

In order to ensure that peptide IV-H1-mediated cell adhesion and spreading was not unique to K1735 M4 melanoma cells, various other cell types were screened for adhesion and spreading on surfaces coated with the peptide. Cells of different embryonic origin and from various species were studied for the ability to adhere and spread on surfaces coated with peptide IV-H1. The cell types comprised three major groups (See Table 2): first, cells which adhere and spread on both peptide IV-H1 and type IV collagen which, in addition to including the murine high metastatic K1735 M4 melanoma, included a highly metastatic human melanoma (A375M), a rat glioma (C6), and a rat neuroblastoma (B104); second, cells which adhered and spread on type IV collagen but not on peptide IV-H1, including bovine aortic endothelial cells and the human squamous carcinoma cell line (SCC9); and third, cells which did not adhere to either type IV collagen or peptide IV-H1, including the murine UV2237 MM fibrosarcoma and the rat B65 neuroblastoma. In all cases, cell adhesion and spreading on surfaces coated with BSA or control peptides was <5%.

TABLE 2

Cell Adhesion and Spreading to Substratum-Bound Peptide IV-H1 or Type IV Collagen

| Cell Types | Species of Origin | Peptide IV-H1* % AD@ | Peptide IV-H1* % SP | Type IV Collagen % AD |
|---|---|---|---|---|
| GROUP 1 | | | | |
| K1735 M4 melanoma | mouse | 22.4 | 70 | 61.9 |
| A375 M melanoma | human | 16.3 | 78 | 50.3 |
| C6 glioma | rat | 35.9 | 82 | 100.0 |
| B104 neuroblastoma | rat | 18.5 | 20 | 18.6 |
| GROUP 2 | | | | |
| Bovine aortic endothelial | bovine | 0.8 | 0 | 52.7 |
| Squamous carcinoma | human | 1.9 | 0 | 39.6 |
| GROUP 3 | | | | |
| UV 2237 fibrosarcoma | murine | 1.1 | 0 | 7.9 |
| B65 neuroblastoma | rat | 4.6 | 0 | 7.7 |

*Surfaces were coated with 100 μl/well of peptide IV-H1 or intact type IV collagen at 100 μg/ml in Voller's carbonate buffer.
@Percent of input cells which adhered or spread as described in Example 1. Data is expressed as the average of three experiments, each experiment performed in triplicate.

EXAMPLE 3

Melanoma Cell Motility on Peptide IV-H1

Figure 4A:
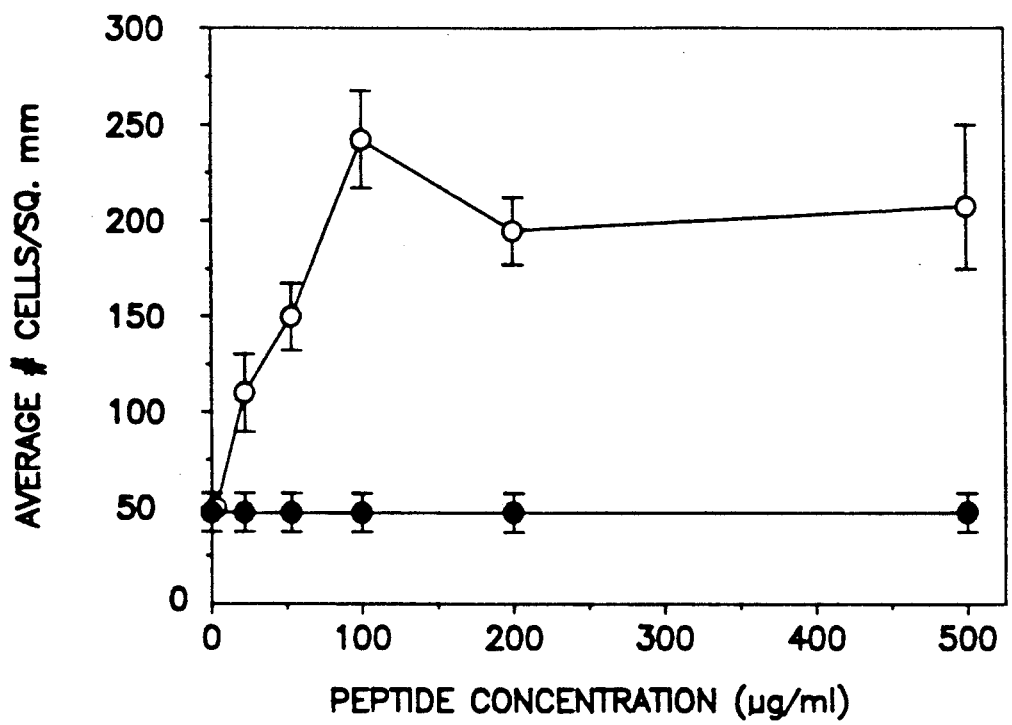
FIG. 4a is a graph showing the average cell motility of melanoma cells in response to peptide IV-H1 (○) and BSA (•) coated on polycarbonate filters.
Figure 4B:
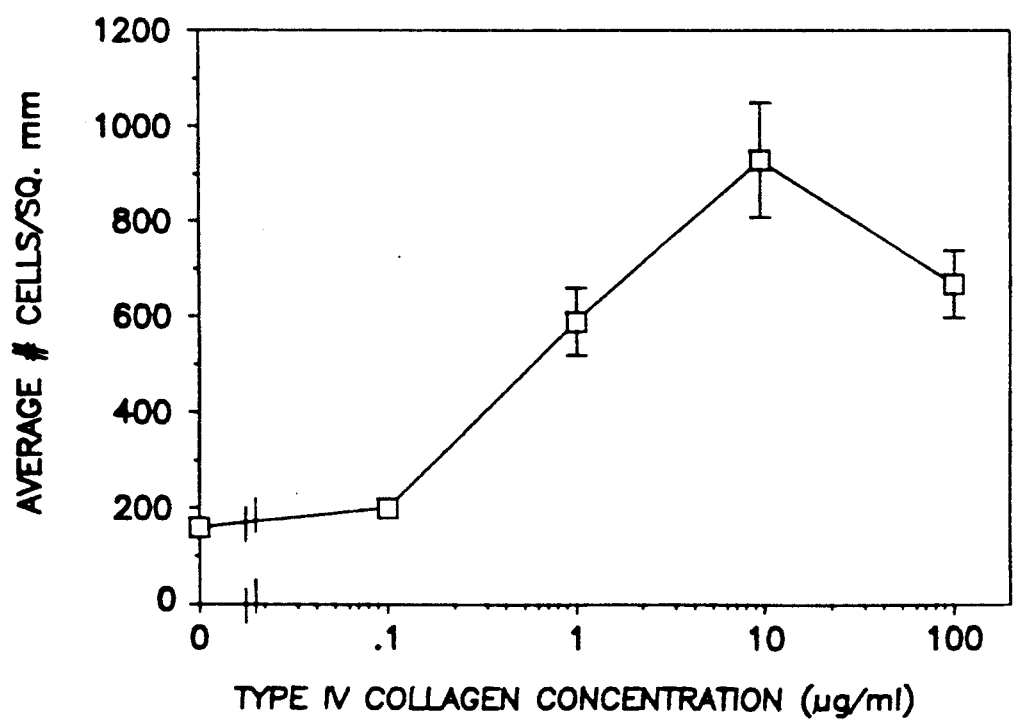
FIG. 4b is a graph showing the number of melanoma cells which migrated across a polycarbonate filter imposed in a Boyden chamber in response to the lower wells of said chamber being filled with Type IV collagen.

In light of the involvement of cell adhesion and spreading in motility, peptide IV-H1 was studied for its ability to directly promote melanoma cell motility. Peptide-mediated M4 melanoma cell motility was examined in 48-well microchemotaxis chambers (Neuroprobe, Bethesda, MD) equipped with 8 μm pore size polyvinylpyrrolidone-free polycarbonate filters by a modification of a procedure described by Herbst et al., supra. Briefly, peptides were diluted in Voller's carbonate buffer and added in triplicate 50 μl aliquots to the lower wells of the chambers. The chambers were assembled with the filters in place and incubated overnight at 37° C. to allow the peptides to adsorb to the lower surfaces of the filters. The filters were then washed and transferred to fresh chambers which contained only media (DME containing 20 mM Hepes, pH 7.4). Cells were then added to the upper wells at 20,000/well in DME/Hepes media and incubated for 6 hr. at 37° C. in a humidified CO$_2$ chamber. Filters were then washed, fixed and stained, and the number of cells which had migrated through the filters was quantitated using an Optomax Image Analysis System as described in Herbst et al., supra. Each experiment was repeated a minimum of three times. The results show that peptide IV-H1 promoted a concentration-dependent increase in melanoma cell motility in microchemotaxis chambers (FIG. 4a). Whereas a significant level of motility (twice BSA control levels) was observed at a coating level as low as 20 μg/ml, maximal cell motility (5 times BSA control levels) was observed when the filter was coated with a 100-200 μg/ml solution of peptide IV-H1. This compares with melanoma cell motility of 10-fold background levels in response to a 10 μg/ml solution of intact type IV collagen (FIG. 4b).

EXAMPLE 4

Inhibition of Cellular Adhesion, Spreadinq and Motility by Exogenous Peptide IV-H1

The ability of excess soluble peptide IV-H1 to inhibit type IV collagen-mediated M4 melanoma cell adhesion, spreading and migration was studied. The specificity of the peptide IV-H1 sequence within type IV collagen was determined by including type I collagen in the inhibition studies. As an additional control, type IV collagen-derived peptide 17 was studied for its ability to inhibit collagen-mediated cell activity. Peptide 17 has a length and amino acid content similar to peptide IV-H1, but does not promote melanoma cell adhesion or spreading. Cells remained viable in the presence of all concentrations of peptides studied, as demonstrated by exclusion of trypan blue dye.

In these examples, Immulon 1 plates were coated as described in Example 1 above, for use in cell adhesion assays using concentrations of peptide IV-H1, type IV collagen or type I collagen (50 μg/ml of the peptide and 5 μg/ml of the intact proteins) which yielded half-maximal M4 melanoma cell adhesion in previous dose-response experiments. The cells were preincubated for 20 min. at 37° C. in the presence (or absence) of various concentrations of the peptides in order to occupy the cell surface binding proteins recognizing these peptides. Spreading and adhesion determinations were quantitated as described in Example 1 above.

The ability of peptide IV-H1 to inhibit type IV collagen-mediated haptotactic motility was determined by precoating filters on the underside with either type IV collagen or type I collagen in Voller's carbonate buffer as described in Example 3 above. The collagen coating concentration (5 μg/ml) was chosen based on the concentration which yielded half-maximal levels of cellular motility. The inhibitory effect of the peptides on cell motility was determined by preincubating the cells with increasing concentrations of the peptides for 20 min. prior to the assay to allow for binding to cell surface receptors. Cells in the continued presence of peptides were then added to the upper wells of chambers containing the protein-coated filters.

Figure 5A:
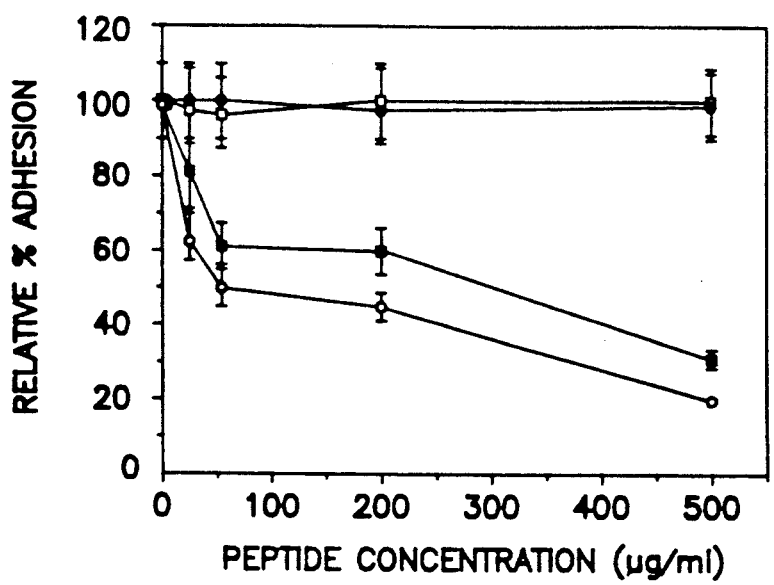
FIG. 5a is a graph showing the relative inhibition of adhesion of melanoma cells to Immulon I wells coated with peptide IV-H1 (○), Type I collagen (□) and Type IV collagen (■) per concentration of excess soluble peptide IV-H1 and coated with Type IV collagen per concentration of excess soluble control peptide 17 (•).

In the adhesion assays, exogenous soluble peptide IV-H1 strongly inhibited IV-H1-and type IV collagen-mediated melanoma cell adhesion (FIG. 5a). Melanoma cell adhesion on surfaces coated with peptide IV-H1 was inhibited by nearly 40% in the presence of soluble peptide IV-H1 at 20 μg/ml, and by 80% at the highest concentration of peptide IV-H1 tested (500 μg/ml) (FIG. 5a). Similarly, melanoma cell adhesion to surfaces coated with type IV collagen was inhibited by 20% in the presence of only 20 μg/ml soluble peptide IV-H1, and by as much as 70% at the highest concentration of peptide studied (500 μg/ml). In contrast, melanoma cell adhesion on surfaces coated with type I collagen was not affected by the presence of soluble peptide IV-H1. In addition, no effect of the control peptide 17 (FIG. 3a) on type IV collagen-mediated melanoma cell adhesion was observed, even at the highest concentration tested (500 μg/ml).

Figure 5B:
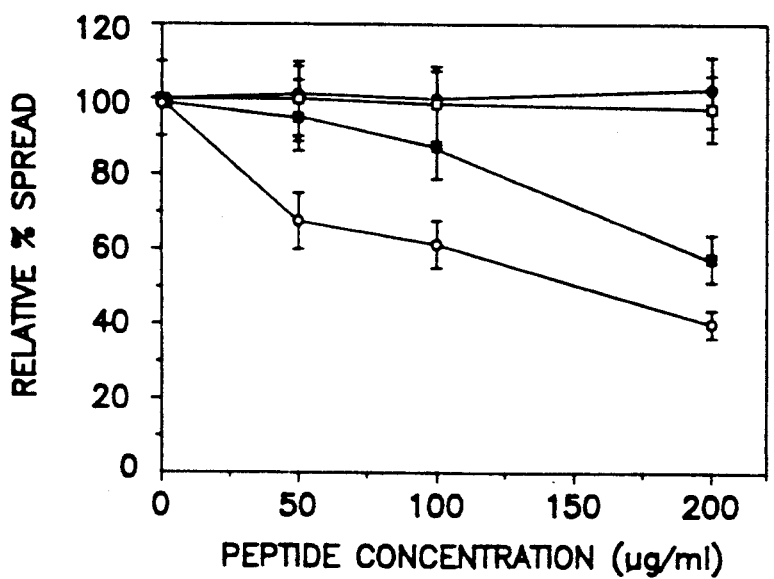
FIG. 5b is a graph showing the relative inhibition of spreading of melanoma cells on Immulon I wells coated with peptide IV-H1 (○), Type I collagen (□) and Type IV collagen (■) per concentration of excess soluble peptide IV-H1 and coated with Type IV collagen per concentration of excess soluble control peptide 17 (•).

Cell spreading on surfaces coated with peptide IV-H1 was inhibited by up to 70% in the presence of soluble peptide IV-H1 at 200 μg/ml (FIG. 5b). Similarly, cell spreading on type IV collagen-coated surfaces was inhibited by 20% at the 100 μg/ml concentration of peptide IV-H1 and the level of cell spreading decreased by 50% at the highest concentration studied (200 μg/ml). In contrast, pretreatment of cells with peptide IV-H1 had no effect on the percent of cells spreading on surfaces coated with type I collagen. In control studies, excess peptide 17 (FIG. 5b) had no effect on cell spreading on surfaces coated with type IV collagen or peptide IV-H1.

Figure 5C:
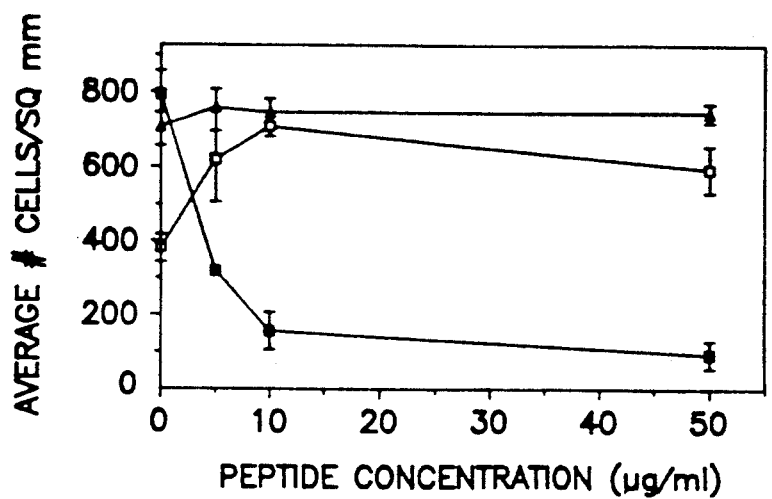
FIG. 5c is a graph showing the inhibition of melanoma cell motility through polycarbonate filters coated with Type IV (■) and Type I (□) collagen, in response to excess soluble peptide IV-H1, and coated with Type IV collagen in response to excess soluble control peptide 17 (△).

Finally, type IV collagen-mediated cell motility was inhibited by peptide IV-H1 in a dose-dependent manner with maximal inhibition of 80% at the 50 μg/ml level of peptide IV-H1 (FIG. 5c). Melanoma cell motility through filters precoated with type I collagen, however, was not inhibited by the presence of peptide IV-H1. Peptide 17 had no effect on type IV collagen-mediated cell motility.

EXAMPLE 5

Polyclonal IqG Inhibition of Type IV Collagen-Mediated Cell Adhesion, Spreading and Motility

A. Generation and Purification of Polyclonal Antibodies

Polyclonal antibodies were generated against peptide IV-H1 coupled to keyhole limpet hemocyanin (KLH: Sigma Chemical Co.) using carbodiimide as a coupling agent, based on a procedure described by Bauminger and Wilchek, *In, Methods in Enzymoloqy*, H. Van Bunakis and J. J. Langone, eds., 70, 151-159 (1980). Briefly, equal amounts (by weight) of peptide and KLH were solubilized in water and mixed with a 10-fold excess (by weight) of 1-ethyl-3(3-dimethlyaminopropyl)- carbodiimide hydrochloride (Sigma Chemical Co.) dissolved in water. New Zealand White rabbits were immunized on the back by multiple intradermal injections of approximately 2 mg. per rabbit of peptide/KLH conjugate in Complete Freund's Adjuvant. Subsequent biweekly boosts were given intramuscularly in Incomplete Fruend's Adjuvant. Sera were collected 14 days following the fourth immunization, and tested by RIA for reactivity against uncoupled peptide, the protein of origin, and various other ligands.

Immunoglobulin G (IgG) was purified from normal rabbit sera and pooled immune sera by precipitation with a final concentration of 50% ammonium sulfate overnight at 4° C. The resolubilized precipitate was dialyzed against 0.035M NaCl in 0.025M Tris, pH 8.8, and the IgG was purified by DEAE column chromatography as described previously (Skubitz et al., 1987). Purity of the IgG was determined by SDS-PAGE. Retained immunoreactivity of the purified IgG was verified by RIA.

B. Assays for IV-H1 Antibody Specificity

Immune sera and purified anti-peptide IV-H1 IgG was screened for specificity by an indirect solid-phase RIA in 96-well polystyrene Immulon 1 plates as described in Skubitz et al., Exp. Cell Res., 173, 349–369 (1987). Briefly, 50 μl of proteins or peptides at various concentrations in Voller's carbonate buffer was added to each well and dried overnight at 29° C. The next day, 200 μl of PBS containing 5% BSA (fraction V, fatty acid free, Sigma Chemical Co.), 0.1% Triton X-100, and 0.02% NaN$_3$ was added to each well followed by a 60 min. incubation at 37° C. After removal of this buffer, 100 μl of purified IgG at various dilutions in PBS containing 5% BSA and 0.02% NaN$_3$, was added in triplicate and the wells were incubated 1 hr. at 37° C. After three washings with the above buffer, bound IgG was detected by the addition of 100 μl of 5% BSA in PBS/NaN$_3$ containing approximately 100,000 cpm of $^{125}$I-labeled donkey IgG directed against rabbit IgG (sp. act. 5 μCi/μg; Amersham, Arlington Heights, Ill). After a 1 hr. incubation at 37° C., unbound antibody was removed by washing. Following an incubation with 100 μl of 2M NaOH for 15 min. at 60° C., the solubilized proteins were transferred to glass tubes and the radioactivity was measured in a Tm Analytic gamma counter model 1193.

Purified IgG generated against KLH-coupled peptide IV-H1 was screened for immunoreactivity by RIA (See Table 3). Reactivity of anti-peptide IV-H1 IgG was type IV collagen-specific, since the IgG recognized type IV collagen and peptide IV-H1 but not type I collagen. The control purified normal rabbit IgG did not react with type IV collagen or any of the synthetic type IV collagen-derived peptides.

C. Effect of Anti-peptide IV-H1 IqG on Collagen-Mediated Cell Adhesion, Spreading and Motility Polyclonal antibodies were generated against peptide IV-H1 and tested for the ability to inhibit type IV collagen-mediated M4 melanoma cell adhesion, spreading and motility. In these assays, Immulon 1 plates were coated as described in Example 1 above for use in cell adhesion assays using concentrations of peptide IV-H1, type IV collagen or type I collagen (50 μg/ml of the peptide and 5 μg/ml of the intact proteins) which yielded half maximal M4 melanoma cell adhesion in previous dose response experiment.

The protein coated surfaces were incubated with various concentrations of purified normal rabbit IgG or purified IgG against peptide IV-H1 in order to block the corresponding sequence within the surface-bound protein. Cells were then dispensed into the wells, in the continued presence of peptide or IgG, and incubated at 37° C. for 30 min. Spreading and adhesion determinations were quantitated as described above.

In addition, the inhibitory effect of anti-peptide IV-H1 IgG on haptotaxis was determined by incubation of the protein-coated filters for 20–30 min. with antibody in the lower wells to bind (and thus block) the IV-H1 sequence within the type IV collagen molecule. Cells were then added to the upper wells and the assay proceeded as described in Example 4 above.

TABLE 3

| Reactivity of Antibody Raised Against Peptide IV-H1 | | | | |
|---|---|---|---|---|
| (Ligand) | IgG Concentration (μg/ml) | | | |
| Protein or Peptide | 0.001* | 0.004 | 0.02 | 1.0 |
| Peptide IV-H1 | 2996@ | 3179 | 3705 | 3927 |
| Type IV collagen | 127 | 290 | 779 | 1747 |
| Type I collagen | 69 | 71 | 110 | 198 |
| Fibronectin | 88 | 73 | 88 | 257 |

*Purified anti-peptide IV-H1 IgG was screened for specificity by an indirect solid-phase RIA. Briefly, surfaces were coated with proteins or peptides as described previously. Purified IgG at various dilutions were added. Bound IgG was detected by the addition of $^{125}$I-labeled secondary IgG (sp. act. 5 μCi/μg).
@Quantitation of $^{125}$I-labeled secondary IgG bound, expressed as cpm.

Figure 6A:
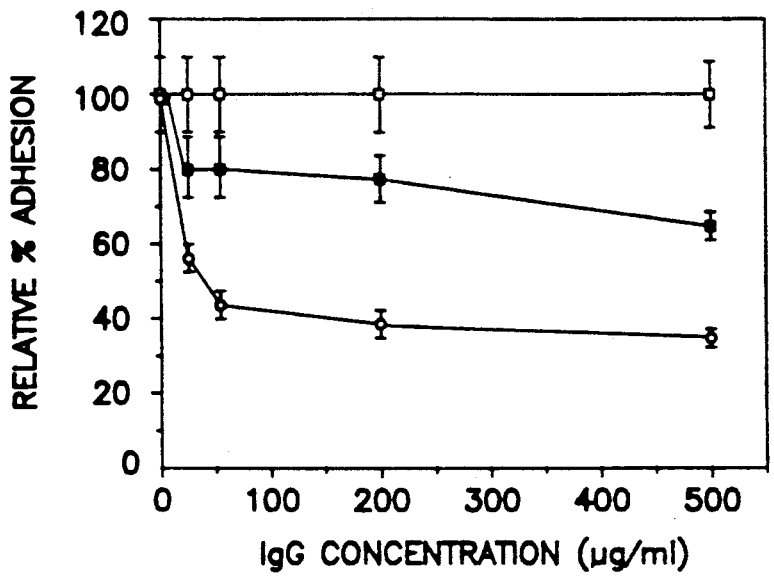
FIG. 6a is a graph showing the relative inhibition of adhesion of melanoma cells to Immulon I wells coated with peptide IV-H1 (○), Type I collagen (□) or Type IV collagen (■) per concentration of Anti-IV-H1 IgG and coated with Type IV collagen per concentration of normal rabbit IgG (▲).

Melanoma cell adhesion on surfaces coated with peptide IV-H1, intact type IV collagen, or type I collagen was monitored in the presence of increasing concentrations of anti-peptide IV-H1 IgG. Melanoma cell adhesion on surfaces coated with 50 μg/ml of peptide IV-H1 was inhibited 40% by anti-IV-H1 IgG at 20 μ/ml (FIG. 6a). Maximal inhibition (70%) was observed at the highest concentration of antibody tested (500 μg/ml). Cell adhesion to type IV collagen was also reduced in a concentration-dependent manner by preincubation with anti-IV-H1 IgG. Significant inhibition (20%) was observed in the presence of only 20 μg/ml of anti-peptide IV-H1 IgG, and a 40% inhibition of adhesion was observed at 500 μg/ml of anti-peptide IV-H1 IgG. In contrast, preincubation with the anti-peptide IV-H1 IgG did not reduce the levels of melanoma cell adhesion to surfaces coated with type I collagen. No inhibition of cell adhesion to surfaces coated with any of the collagenous proteins was observed in the presence of normal rabbit IgG, even at the highest concentrations used (500 μg/ml); demonstrated by the lack of inhibition of cell adhesion to peptide IV-H1 with normal rabbit IgG (FIG. 6a).

Figure 6B:
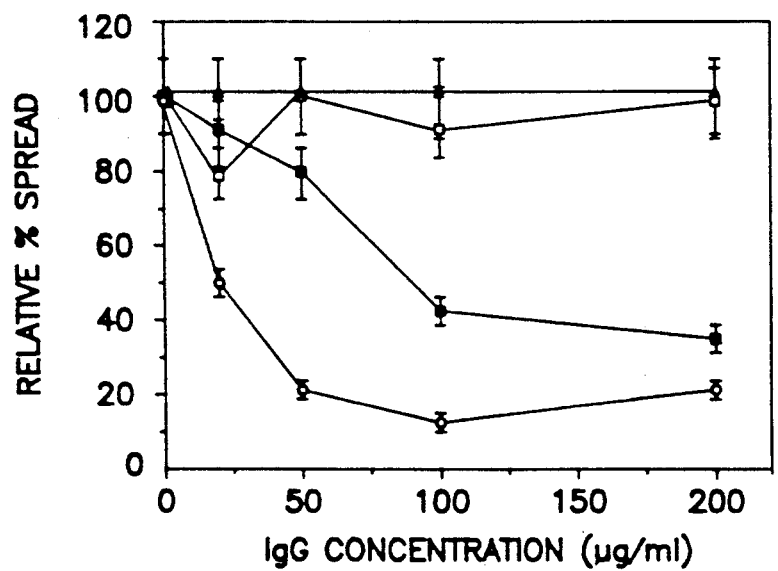
FIG. 6b is a graph showing the relative inhibition of spreading of melanoma cells on Immulon I wells coated with peptide IV-H1 (○), Type I collagen (□) or Type IV collagen (■) per concentration of Anti-IV-H1 IgG and coated with Type IV collagen per concentration of normal rabbit IgG (▲)

Melanoma cell spreading on surfaces coated with peptide IV-H1, intact type IV collagen, or type I collagen was monitored in the presence of increasing concentrations of anti-peptide IV-H1 IgG. Cell spreading on surfaces coated with peptide IV-H1 was significantly decreased (50%) at levels of anti-peptide IV-H1 IgG as low as 20 μg/ml, and maximal inhibition (80%) was observed at 50 μg/ml (FIG. 6b). Similarly, cell spreading on surfaces coated with type IV collagen was decreased by 20% in the presence of 50 μg/ml of anti-peptide IV-H1 IgG and by as much as 60% when 100 μg/ml of this IgG was present. In contrast, cell spreading on surfaces coated with type I collagen was not affected by this IgG (FIG. 6b). The control normal rabbit IgG did not affect cell spreading on surfaces coated with peptide IV-H1, type IV collagen, or type I collagen.

Figure 6C:
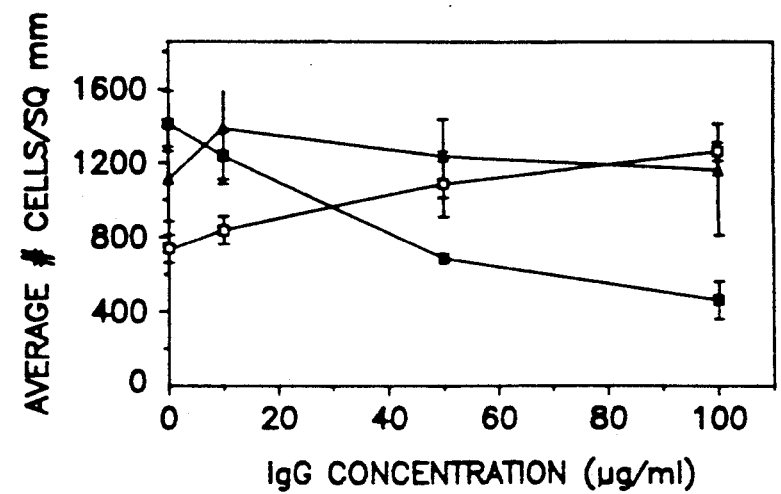
FIG. 6c is a graph showing the inhibition of melanoma cell motility on polycarbonate filters coated with Type I collagen (□) and Type IV collagen (■) in response to Anti-IV-H1 IgG and coated with Type IV collagen in response to normal rabbit IgG (▲).

The effect of anti-peptide IV-H1 IgG on melanoma cell haptotaxis mediated by type IV collagen was monitored by incubating the collagen-coated filter with anti-peptide IV-H1 IgG prior to the addition of cells to the motility assay (FIG. 6c). Motility was decreased in a concentration-dependent manner with maximal inhibition of 70% at 100 μg/ml of IgG. In contrast, cell motility through filters precoated with type I collagen (FIG. 6c) was not inhibited by preincubation of the filters with anti-peptide IV-H1 IgG. Normal rabbit IgG had no effect on type IV collagen-mediated cell motility.

EXAMPLE 6

Binding of Peptide IV-H1 to Neural Cells

Dorsal Root Ganglia were isolated surgically from 9-day chick embryos. Connective tissue was removed from the neural tissue, both surgically and enzymatically. The remainder of isolated cells included neurons, glial cells, and residual fibroblasts. Cells were then diluted to 40,000 cells per milliliter of media. 0.5 ml of the cell suspension was added to the wells of 24 Immulon I plates which had been coated as shown in Example I above, with peptide IV-H1, as well as various positive and negative controls.

Figure 7:
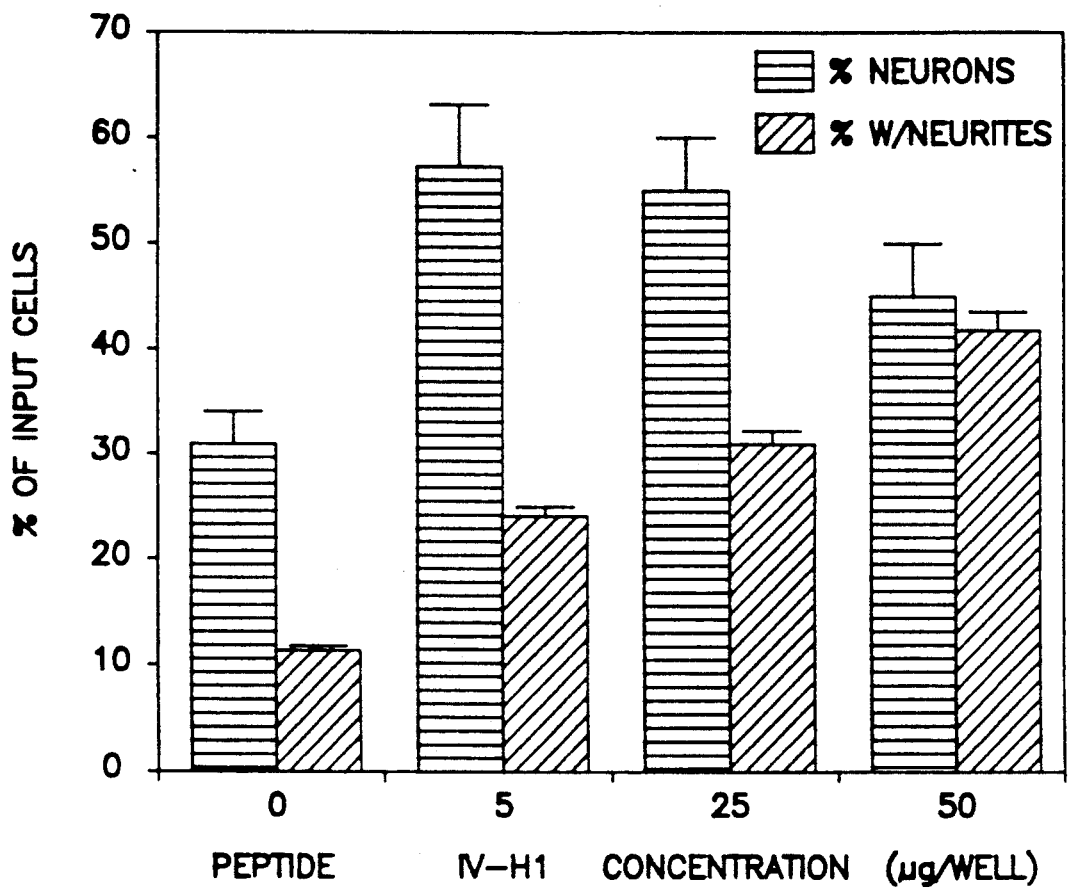
FIG. 7 is a graph showing the percent of chick neurons adhering to Immulon I wells coated with varying concentrations of peptide IV-H1, and the percent of the adherent neurons with extended neurites per concentration of peptide IV-H1.

The assay was incubated in a 37° C. humidified incubator for 24 hours. The media was then removed and the plates were washed to remove nonadherent cells. Adherent cells were fixed using a 1% glutaraldehyde solution. Quantification of the number of neurons which adhered to the surfaces as well as the number of neurons extending neurites was done by two individuals, under double blind conditions. The results show that neuron adhesion and neurite extension were promoted in a concentration dependent manner. (FIG. 7). A concentration of 5 μg/ml of peptide IV-H1 resulted in maximal cell adhesion, while 50 μg/ml caused the highest extension of neurites from adherant neurons.

These results taken together indicate that peptide IV-H1 is a major participant in the process of tumor cell adhesion, spread and motility, and is highly specific as to the cell type with which it will bind.

A number of practical applications for the polypeptide of the present invention can be envisioned. Such applications include the ability to inhibit metastasis and invasion of malignant cells, use as a diagnostic tool, and to promote the regeneration of nerves.

In the past, selected laminin domains have been studied for ability to decrease the metastatic potential of invasive cell lines [McCarthy et al., *Cancer Met. Rev.*, 4, 125-152 (1985)]. This effect is mediated via the saturation and therefore neutralization of cell surface receptors for laminin. In accordance with the present invention, the data presented herein suggest that receptors for the polypeptide IV-H1 from type IV collagen exist on cell surfaces of malignant cells. Consequently, excess soluble polypeptide or polyclonal IgG antibodies of peptide IV-H1 could be used to block type IV collagen receptors of metastatic cells and therefore reduce their metastatic potential. In addition, peptide IV-H1 coupled to an appropriate chemotherapeutic agent could be used to diagnose and treat malignant cell growths.

Also, the peptide of the present invention may prove useful to facilitate regeneration of damaged nerve tissue. In particular, peptide IV-H1 favors nerve cell outgrowth since the peptide promotes the adhesion only of cells of neural crest origin. For example, neurons adhere, but endothelial cells do not. Thus, the binding specificity of the peptide precludes endothelial cells from interfering with the artificial nerve growth.

The invention has been described with reference to various specific and preferred embodiments and techniques. However, it should be understood that many variations and modifications may be made while remaining within the spirit and scope of the invention.

What is claimed is:

1. A polypeptide having an amino acid sequence corresponding substantially to amino acid residues 1263 through 1277 of the continuous collagenous region of the major triple helical domain of the α1 chain of type IV collagen, wherein said polypeptide promotes cellular adhesion and spreading, and further wherein said polypeptide has an amino acid sequence of about 15 residues.

2. The polypeptide of claim 11 wherein said polypeptide has the formula:

gly—val—lys—gly—asp—lys—gly—asn—pro—gly—trp—pro—gly—ala—pro.

* * * * *

UNITED STATES PATENT AND TRADEMARK OFFICE
CERTIFICATE OF CORRECTION

PATENT NO. : 5,082,926

DATED : January 21, 1992

INVENTOR(S) : Mary K. Chelberg et al.

It is certified that error appears in the above-identified patent and that said Letters Patent is hereby corrected as shown below:

At column 1, line 20, for "N.Y.," read --NY,--

At column 1, line 64, for "noncollagenous" read --non-collagenous--

At column 3, line 57, after "260" insert --,--

At column 4, line 24, for "Ill," read --IL--

At column 6, line 26, for "Calif." read --CA.--

At column 6, line 36, for "Mass.)." read --MA).--

At column 6, line 40, for "Mass.)," read --MA),--

At column 6, line 46, for "Va.)" read --VA)--

At column 10, line 32, for "IqG" read --IgG--

At column 11, line 22, for "Ill)." read --IL).--

UNITED STATES PATENT AND TRADEMARK OFFICE
CERTIFICATE OF CORRECTION

PATENT NO. : 5,082,926

DATED : January 21, 1992

INVENTOR(S) : Mary K. Chelberg et al

It is certified that error appears in the above-identified patent and that said Letters Patent is hereby corrected as shown below:

At column 11, line 39, for "IqG" read --IgG--.

Signed and Sealed this

Thirtieth Day of November, 1993

Attest:

BRUCE LEHMAN

Attesting Officer

Commissioner of Patents and Trademarks